United States Patent [19]

Esders et al.

[11] 4,444,886

[45] Apr. 24, 1984

[54] DIACETINASE FROM *BACILLUS SUBTILIS*

[75] Inventors: Theodore W. Esders, Webster; Charles T. Goodhue, Rochester; Ohannes K. Esmerian, Pittsford, all of N.Y.

[73] Assignee: Eastman Kodak Company, Rochester, N.Y.

[21] Appl. No.: 407,213

[22] Filed: Aug. 11, 1982

[51] Int. Cl.$^3$ .......................... C12N 9/20; C12N 9/18; C12R 1/125

[52] U.S. Cl. .................................... 435/198; 435/197; 435/839

[58] Field of Search ................................ 435/198, 197

[56] References Cited

U.S. PATENT DOCUMENTS 3,634,195  1/1972  Melachouris et al. .
4,275,166  6/1981  McCollough et al. .

FOREIGN PATENT DOCUMENTS 53-069878 of 0000 Japan .

OTHER PUBLICATIONS

T. B. Higerd and J. Spizizen, "Isolation of Two Acetyl Esterases from Extracts of *Bacillus Subtilis*," *Journal of Bacteriology*, vol. 114, No. 3, Jun. 1973, pp. 1184–1192.

*Primary Examiner*—Lionel M. Shapiro
*Attorney, Agent, or Firm*—J. Lanny Tucker

[57] ABSTRACT

An enzyme which catalyzes the hydrolysis of glycerol esters is disclosed. The enzyme is specific for alkyl esters wherein the alkyl group has from 1 to 4 carbon atoms inclusive. The enzyme is particularly useful in hydrolyzing a diacetyl glycerol ester. The enzyme is from the microorganism *Bacillus subtilis* ATCC No. 31954.

4 Claims, No Drawings

DIACETINASE FROM *BACILLUS SUBTILIS*

BACKGROUND OF THE INVENTION

CROSS-REFERENCE TO RELATED APPLICATIONS

The present invention is related to the invention disclosed and claimed in commonly assigned U.S. Ser. No. 407,214 to LiMuti, Babb and Mauck entitled METHODS, COMPOSITIONS AND ELEMENTS FOR THE DETERMINATION OF LIPASE.

FIELD OF THE INVENTION

The present invention relates to an enzyme which catalyzes the hydrolysis of glycerol esters. This type of enzyme is referred to in the art as an esterase or more specifically a glycerol ester hydrolase.

DESCRIPTION OF RELATED ART

As noted above, the present invention is related to U.S. Ser. No. 407,214 to LiMuti, Babb and Mauck. That application describes an analytical method for the determination of lipase. In the first step, the lipase in the sample catalyzes the hydrolysis of a long-chain ester in the α position of a glycerol triester. The substrate is such that the alkyl groups on the resulting diester are short-chain alkyl groups. In the next step of the process, the short-chain alkyl groups are hydrolysed so as to produce glycerol. The rate of formation of glycerol is detected and is related to the lipase in the sample.

The hydrolysis of the short-chain alkyl groups is catalyzed by an esterase enzyme which is specific for short-chain alkyl groups. Many of these esterase enzymes are known in the art and are useful in the practice of the described process.

Esterase enzymes from *Bacillus subtilis* are known. For example, Higerd and Spizizen describe two of these enzymes ("Isolation of Two Acetyl Esterases from Extracts of *Bacillus subtilis*, *J. of Bacteriology*, 114, pages 1184–1192 (1973)). The enzymes from the strains described in this reference were produced in less than desired quantities (see comparative example 7). Further, gel electrophoresis of these enzymes in comparison with the enzyme of the present invention conclusively showed that the enzyme of the present invention is different from either of the enzymes disclosed in the reference. Details regarding the electrophoresis experiment are found later in the specification in comparative example 8.

After the invention described in U.S. Ser. No. 407,214 was made, it became apparent that improvements in the esterase enzyme would be desirable. While known enzymes are useful, the rate of the catalyzed reaction was slower than desired. Furthermore, many known esterase enzymes lacked the desired specificity. For example, if stored in contact with the lipase substrate for long periods, many of these prior-art enzymes eventually catalyze the hydrolysis of the long-chain alkyl group in the α position of the substrate. This, of course, seriously affects the sensitivity of the method because much of the starting substrate is used up through this mechanism. A new enzyme which is highly specific and which has high activity is desirable. Further, it is desirable to find a source which produces large amounts of enzyme.

SUMMARY OF THE INVENTION

We have discovered a new enzyme which catalyzes the hydrolysis of glycerol esters. The enzyme is isolated from the microorganism *Bacillus subtilis* ATCC No. 31954. The enzyme is highly specific for short chain alkyl groups (1–4 carbon atoms). The enzyme is particularly useful because the hydrolysis in the presence of this enzyme, is rapid and because large amounts of the enzyme are produced by this microorganism.

In another aspect of the invention, there is provided a method for the production of an enzyme which catalyzes the hydrolysis of glycerol esters wherein the alkyl group has from 1 to 4 carbon atoms inclusive comprising the steps of:
 (a) growing the microorganism *Bacilus subtilis* ATCC No. 31954 in a growth medium and
 (b) recovering the enzyme therefrom.

The enzyme is particularly useful as the diesterase in the invention of LiMuti, Babb and Mauck described above.

DETAILED DESCRIPTION OF THE INVENTION

The microorganism which produces the enzyme of the invention is a strain of *Bacillus subtilis*. This strain was isolated from a soil sample obtained near Rochester, New York. A sample of the isolated strain has been deposited with the American Type Culture Collection, and has been given the identification number ATCC No. 31954.

The microorganism from which the diesterase is recovered is preferably grown on what is known in the art as MRS medium. This medium is described by DeMann et al, "A Medium for the Cultivation of Lactobacilli," J. App. Bact., 23 (1), 130–135.

After fermentation, the diesterase is recovered from the growth medium using known enzyme recovery processes. The enzyme is an intracellular enzyme. Generally, the enzyme is recovered by disrupting the cells and then recovering the enzyme, preferably by precipitation with an organic solvent such as n-propanol. Useful processes are described in U.S. Pat. Nos. 3,597,323, 4,087,329, 4,134,793 and 4,275,166.

In the Examples, the following materials and procedures were used:

A. Materials

Egg-white lysozyme, deoxyribonuclease (DN-100) from bovine pancreas, ribonuclease A from bovine pancreas (Type 1-A), triolein and gum arabic were purchased from Sigma Chemical Co., St. Louis, Mo. Bacto® yeast extract was obtained from Difco Labs, Detroit, Mich. DeMann, Ragossa and Sharpe (MRS) broth (CM 359), yeast extract, Lab Lemco® powder (L-29) (meat extract nutrient broth), peptone (L-34), and Oxoid agar III® were purchased from Oxoid Canada Ltd. Ottawa, Ontario, Canada. Polyglycol (P-2000)® was obtained from Dow Chemical Co., Midland, Mich. Diacetin, glucose and other chemicals, unless otherwise specified, were obtained from Eastman Organic Chemicals, Rochester, N.Y.

B. Media

MRS Medium

| | Per Liter |
|---|---|
| peptone (L-34) | 10.0 g |
| Lab Lemco ® powder (L-29) | 8.0 g |
| yeast extract (Oxoid) | 4.0 g |
| glucose | 20.0 g |
| Tween ® 80 surfactant | 1.0 mL |
| potassium hydrogen phosphate (K$_2$HPO$_4$) | 2.0 g |
| sodium acetate trihydrate | 5.0 g |
| triammonium citrate | 2.0 g |
| magnesium sulfate heptahydrate | 0.2 g |
| manganese sulfate tetrahydrate | 0.05 g |
| agar (Oxoid III ®) | 20.0 g |

The pH was adjusted to 6.2 with dilute sulfuric acid.

Diacetin-Containing MRS Medium

| | Per Liter* |
|---|---|
| MRS medium described above | 72.25 g |
| diacetin (filter sterilized) | 2.0 mL |

Salt Solution C (Modified)

| | Per Liter |
|---|---|
| sodium chloride (NaCl) | 0.6 g |
| calcium chloride dihydrate | 0.1 g |
| ferric sulfate heptahydrate | 2.8 g |
| sodium molybdate dihydrate | 0.1 g |
| zinc sulfate heptahydrate | 0.06 g |
| manganese sulfate monohydrate | 1.7 g |
| Magnesium sulfate heptahydrate | 25.0 g |

*The starting solution was 0.1 N hydrochloric acid.

Yeast Extract Medium

| | Per Liter |
|---|---|
| ammonium sulfate | 2.0 g |
| potassium hydrogen phosphate (K$_2$HPO$_4$) | 2.0 g |
| yeast extract (Bacto) | 5.0 g |
| salt solution C (modified) | 10.0 mL |

The pH was adjusted to 6.9 with dilute sulfuric acid.

Diacetin-Containing Yeast Extract Medium

| | Per Liter |
|---|---|
| yeast extract medium (described above) | 9.0 g |
| diacetin (filter sterilized) | 2.0 mL |

Pyruvate Medium (PM)

| | Per Liter |
|---|---|
| sodium pyruvate | 10.0 g |
| yeast extract | 5.0 g |
| potassium hydrogen phosphate (K$_2$HPO$_4$) | 2.0 g |
| salt solution C (modified) (described above) | 10.0 mL |

The pH was adjusted to 4.5 with 6 N hydrochloric acid.

C. Procedures

1. Isolation of Bacillus subtilis

The culture was isolated from soil samples by enrichment in the pyruvate medium, described above, at 40° C. Ten frozen soil samples were thawed. Approximately 10 g each of the soil samples were added to 125 mL flasks, containing 25 mL of pyruvate medium. The flasks were incubated at 40° C. without shaking. When the media became turbid, in about 3 days, 0.5 mL of each was transferred to test tubes containing 10 mL of pyruvate medium. After several days of incubation at 40° C. without shaking, each test-tube culture was diluted 10:1, plated out on pyruvate medium and MRS medium, which was supplemented with pyruvate at 0.25 percent and then incubated for 24–48 hr. Of these cultures, isolate ATCC No. 31954 was chosen.

2. Taxonomic Data

The following publications on the taxonomy of *Bacillis* microorganisms were used as guides to identify the isolate: R. E. Gordon, *CRC Handbook of Microbiology*, Vol. I, A. I. Faskin and H. A. Leichevalier, editors, CRC Press, Cleveland, Ohio, 1973, page 71, and T. Gibson and R. E. Gordon, *Bergy's Manual of Determinative Bacteriology*, 8th edition. R. E. Buchanan and N. E. Gibbons, editors, The Williams and Wilkins Co., Baltimore, Md., 1974, page 529. The responses of isolate ATCC No. 31954 most closely resembled the published responses of *Bacillus subtilis* and the responses of a control culture *Bacillus subtilis* (Ward's 85WO228).

Isolate ATCC No. 31954 was an aerobic, gram-positive, spore-forming, motile rod, 2–3$\mu \times 0.5\mu$. The majority of the cells were single when grown in MRS medium; a few were doublets and a few filaments, as long as 50$\mu$, were present. Cells grown on slants yielded many spores, shown to be centrally positioned. They were elliptical or cylindrical in shape and did not distend the sporangium. Colony morphology was variable: circular, rhizoid or irregular. The edge was either entire, undulate or lobate, while elevation was flat and sometimes umbonate. Surfaces were either smooth or wrinkled. The features of the colonies varied with the composition of the media.

Isolate ATCC No. 31954 did not grow at 5° C. Under anaerobic conditions, insignificant growth was seen on MRS plates. At 55° C., it grew on pyruvate and MRS plates, but not as well as at 40° C. Control cultures of *Bacillus subtilis* (Ward's 85WO228), *Bacillus cereus* (Ward's 85WO200) and *Bacillus megaterium* (ATCC 25300) were evaluated in the same manner as the isolate. The isolate was identified as a strain of *Bacillus subtilis*.

No acid was formed in 48 hr from adonitol, dulcitol, galactose, lactose, levulose, maltose, mannose, raffinose, inositol, trehalose, sorbitol, glucose, cellobiose, rhamnose, melibiose and sucrose. Acid formed slowly from xylose after 48 hr.

Acid, but no gas, was formed from salicin, arabinose, mannitol and glycerol. The strain was further characterized by the following tests:

| | |
|---|---|
| oxidase | positive |
| catalase | positive |
| indole | negative |
| o-nitro phenol galactoside | positive |
| arginine dihydrolase | negative |
| lysine decarboxylase | negative |
| ornithine decarboxylase | negative |
| citrate | negative |
| H$_2$S | negative |
| urea | negative |
| Voges-Proskauer (VP) | positive |
| phenyl alanine | negative |
| nitrate reductase | positive |
| malonate | negative |

Isolate ATCC No. 31954 also hydrolyzed gelatin and esculin. It grew on diacetin and tyrosine, hydrolyzed starch and peptonized litmus milk without reduction. It did not grow on hippurate.

3. Maintenance and Growth of Cultures

Cultures were maintained on MRS medium. The MRS slants were incubated at 40° C. in a rotary shaker-incubator and transferred weekly.

Growth of bacterial cultures was accomplished by placing 50 mL of the various culture media, described above, in 250-mL conical flasks, inoculating with cells from MRS slants above, and incubating in the Psycrotherm at 40° C. and 200 rpm (2-inch throw) for 12 hr.

4. Disruption of Microbial Cells and Preparation of Cell-Free Extracts

Microbial cells were disrupted by lysozyme treatment according to the following procedure: A lysis reagent was prepared which contained 1 mg/mL lysozyme, 0.1 mg/mL deoxyribonuclease, and 0.1 mg/mL ribonuclease in 0.05 M potassium phosphate buffer at pH 7.0. A typical batch of cells from 6.6 L of medium had a wet weight of 50 g. This cell paste was suspended in 250 mL of lysis reagent (17 percent suspension) and brought to 37° C. and incubated at that temperature for 30 min in a metabolic shaker rotating at 150 rpm. Cell-free extract was prepared by centrifugation at 39,000 xg for 10 min in a refrigerated centrifuge.

5. Production of the Enzyme

Seven liters of yeast extract medium were prepared as described above. Six fractions of medium, 1 liter each, were placed in fernbach flasks and 1 drop of polyglycol antifoam added to each. Fifteen fractions of medium, 50.0 mL each, were placed in 250-mL conical flasks. All were autoclaved for 30 min. When the flasks cooled to 40° C., sterilized diacetin was added to the fernbach flasks (2.0 mL each) and to the conical flasks (5 drops each).

Each of two conical flasks above were inoculated with one loopful of *Bacillus subtilis* ATCC No. 31954 from an MRS slant (2-3 days old). The flasks were incubated in the shaker-incubator at 40° C. and 200 rpm for 12 hr.

The flask with the best growth, i.e., most turbid, was used to inoculate 12 of the remaining flasks. Each of the 12 flasks was inoculated with 2.0 mL of inoculum and incubated as described above. Each of the 6 fernbach flasks was then inoculated with 2 flasks which were then incubated in the Psycrotherm at 40° C. for 12 hr.

A fraction was obtained from each fernbach flask and 1:10 dilutions were made. The optical density of each was read at 660 nm. Cells were collected by centrifugation on a refrigerated centrifuge at 0°–4° C. and 9000 rpm for 15 min and then stored frozen.

6. Partial Purification of the Enzyme

Disruption of microbial cells was carried out by lysozyme treatment as described above. After lysis, the total (initial) volume of the suspension was measured. The suspension was stirred in an ice bath until the temperature of the suspension was below 10° C. Then, over a 15-min period, without removing cell debris, cold n-propanol (−20° C.) was added to a concentration of 40 percent (V/V). The mixture was allowed to stir for 20 min after the last addition, then centrifuged at 10,000 rpm at 5° C. for 10 min. The pellet (from the 40 percent propanol fraction) was removed and the clear yellow supernatant again placed in an ice bath and stirred. Again, over a 15-min period, cold n-propanol was added, bringing the n-propanol concentration to 60 percent (V/V). The mixture was allowed to stir for 30 min and then centrifuged as described above. The small yellow pellets (from the 40-60 percent propanol fraction) were collected, placed in a beaker, and suspended in cold (5° C.) 0.05 M potassium phosphate buffer, at pH 7.0, by stirring for 45 min. The cloudy suspension was centrifuged at 39,000 xg at 5° C. for 10 min to clarify. The clear, slightly yellow product was stored frozen.

7. Measurement of the Enzyme

Measurements of enzyme activity were made using pH-Stat ® instrumentation (Radiometer, Copenhagen). Standard reaction mixtures contained, in a total volume of 5.0 mL, 5 μmoles calcium chloride (1 mM) and substrates at various concentrations noted in the Examples below. The pH was adjusted to pH 7.5, and mixtures were equilibrated at 37° C. Reaction was initiated by enzyme addition and then the pH maintained at pH 7.5 by addition of 10.4 mM sodium hydroxide. A blank rate was determined, and hydrolytic activity in each case was calculated from the net linear rate of addition of sodium hydroxide. One unit was that amount of enzyme which catalyzed the production of 1 μmole of acid (addition of 1 μmole NaOH) per min at 37° C. and pH 7.5.

The following Examples are presented to illustrate the invention.

EXAMPLE 1

Growth of Microorganism and Production of Esterase Using Various Media

A. Yeast Extract Media

The *Bacillus subtilis* ATCC No. 31954 microorganism was grown in medium (a) yeast extract and medium (b) diacetin-containing yeast extract (both described above) according to the following procedure:

Fifty mL of medium (b) was inoculated with one loopful of *Bacillus* culture from an MRS slant and incubated in the shaker-incubator at 40° C. and 200 rpm for 12 hr. Two mL of this 12-hr culture broth was used to inoculate conical flasks containing 50 mL of medium (a) and medium (b). These flasks were incubated as described above.

Microbial cells were isolated by centrifugation at 9000 rpm for 20 min at 0°–4° C. using a Sorvall ® RC-2B refrigerated centrifuge.

B. MRS Media

Part A was repeated except that the culture was grown in medium (c) MRS and medium (d) diacetin containing MRS.

Enzyme purification and assays were done as described above. The results tabulated in Table 1 indicate that medium (c) provided the best overall growth and enzyme production.

TABLE 1

|  | Cell Growth | Activities Enzyme Production | |
|---|---|---|---|
|  | (g wet wt/L) | (U/L) | (U/g wet wt) |
| (a) yeast extract | 4.4 | 99 | 22.4 |
| (b) yeast extract + diacetin | 8.8 | 555 | 63.0 |
| (c) MRS | 8.4 | 657 | 78.0 |
| (d) MRS + diacetin | 5.6 | 371 | 68.0 |

EXAMPLE 2

Kinetic Studies of Cell Growth and Esterase Production Using the Preferred MRS Medium The incubation time for maximum cell growth and esterase production on the MRS medium was determined according to the following procedure: Fifty mL of medium were placed in a 250-mL conical flask and inoculated with one loopful of *Bacillus subtilis* ATCC No. 31954. The culture was incubated in the shaker-incubator at 40° C. and 200 rpm for 12 hr. Two mL of this culture was used to inoculate each of eight additional 250-mL conical flasks containing 50 mL of medium which were subsequently incubated, as described above. Each of four fernbach flasks, containing 1 L of medium and 1 drop of P-2000 ® antifoam, was inoculated with two 250-mL conical flasks containing the above culture. The fernbach flasks were incubated in the shaker-incubator at 40° C. and 150 rpm. The cultures were harvested, at the times shown in Table 2, by centrifugation in a centrifuge at 0°–4° C.and 9000 rpm for 20 min.

Partial purification was carried out, as described above. As shown in Table 2, an incubation time of 11 hr resulted in the best cell growth and esterase production in the MRS medium.

TABLE 2

| Incubation Time (Hr.) | Cell Growth (g wet wt/L) | Activities Enzyme Production | |
|---|---|---|---|
| | | (U/L) | (U/g wet wt) |
| 10 | >8.68* | — | 114.5 |
| 11 | 14.01 | 1623 | 127.4 |
| 12 | 13.80 | 1382 | 110.4 |
| 13 | 13.19 | 1215 | 101.4 |

*200-300 mL of culture medium lost during centrifugation

EXAMPLE 3

Partial Purification of the Microbial Esterase from Diacetin Containing Medium

Partial purification of the microbial esterase was carried out using the propanol fractionation method described above. Bacterial cells (53.5 g) were cultured in 6.6 L of the diacetin-containing yeast extract medium. Fifty mL of 0.05 M potassium phosphate buffer was used to suspend the esterase pellets, and the suspension was centrifuged to isolate the purified enzyme.

The results presented in Table 3 show the yields from several different preparations, ranging from 63–72 percent.

TABLE 3

| Reproducibility of Propanol Fractionation Procedure | | | | |
|---|---|---|---|---|
| Pre-para-tion | Diacetinase Activity (Total Units) | | Yield % | Specific Activity of Propanol Pro-duct (U/mg) | Enzyme Activity in Medium (U/L) |
| | Cell-Free Extract* | Propanol Product | | | |
| 1 | 3348 | 2402 | 72 | 6.20 | 507 |
| 2 | 3573 | 2243 | 63 | 7.20 | 541 |
| 3 | 3476 | 2470 | 71 | 4.60 | 527 |
| 4 | 3030 | 2130 | 70 | 6.52 | 459 |

*To measure the amount of activity in the cell-free extract, a 1 mL aliquot of the lysed cell suspension was centrifuged prior to alcohol addition.

EXAMPLE 4 pH Optimum of the Enzyme

Enzyme activity was determined, as described above, at various pH values ranging from 6.0–9.0. Substrate emulsions were prepared using triacetin (25 mM) and tributyrin (16.5 mM). The pH profiles were similar, with a broad optimum from 7.0 to 9.0.

EXAMPLE 5

Substrate Specificity of the Microbial Esterase

To determine substrate specificity of the esterase, triglyceride substrates of various chain lengths at concentrations shown in Table 4 were prepared and evaluated.

The results, shown in Table 4, demonstrate that increases in lipid chain length dramatically decreased the rates of hydrolysis, i.e., resulted in decreased activities and substantiated that the microbial enzyme is specific for short-chain esters.

TABLE 4

| Substrate Specificity of the Enzyme | | |
|---|---|---|
| Substrate | Concentration | Enzyme Activity (U/mL) |
| triacetin | 25.6 mM | 10.28 |
| tributyrin | 16.5 mM | 4.41 |
| trihexanoin | 25.9 nM | 0.60 |
| trioctanoin | 21.2 mM | 0.05 |
| triolein | 5.6 mM | 0.0 |
| oleyl diacetin | 20.0 mM | 0.0 |

EXAMPLE 6

Substrate Affinity of Diacetinase

To determine the affinity of diacetinase for short-chain fatty-acid esters of glycerol, the activity of the enzyme was measured, with the following acetins as substrates: triacetin, diacetin and monoacetin.

Normal hyperbolic curves were obtained for each substrate when the enzyme activities were plotted versus the corresponding substrate concentrations. Based on molar substrate concentration, the highest substrate affinity was observed with triacetin. However, after normalizing the $K_m$ values for the concentration of ester linkages hydrolyzed for each substrate, the affinities were more similar, as shown in Table 5.

TABLE 5

| Michaelis-Menton Constants of the Enzyme for Acetins | | |
|---|---|---|
| Substrate | Diacetinase $K_m$, mM | Diacetinase Normalized $K_m$, mM |
| triacetin | 0.61 | 1.83 |
| diacetin | 1.06 | 2.12 |
| monoacetin | 2.78 | 2.78 |

EXAMPLE 7

Growth of the Microorganism Bacillus subtilis 168 (Higerd) and Production of Esterase in MRS Medium This is a comparative example.

A. The Bacillus subtilis 168 microorganism, isolated by T. B. Higerd et al (T. B. Higerd and J. Spizizen, "Isolation of Two Acetyl Esterases from Extracts of Bacillus subtilis," Journal of Bacteriology, 114:1184–1192, 1972) was grown on an MRS medium, as described above, to compare the esterase yield with the esterase yields obtained when a soil Bacillus subtilis (ATCC No. 31954) was grown on the same medium. The growth and enzyme production and purification procedures described above were followed.

The results, shown in Table 6 below, demonstrate a 29-fold increase in esterase yield from the Bacillus subtilis (ATCC No. 31954) as compared with the 168 strain.

TABLE 6

| Micro-organism | Temperature (°C.) | Incubation Time (hours) | Cell Growth (g wet wt./L) | Enzyme Production | |
|---|---|---|---|---|---|
| | | | | (U/L) | (U/g wet wt.) |
| Bacillus subtilis 168 | 40 | 12 | 9.0 | 22.5 | 2.5 |
| Bacillus subtilis ATCC No. 31954 | 40 | 12 | 8.4 | 657 | 78.2 |

B. Part A was repeated except that the cultures were grown at 25° C. in the MRS medium. The results, shown in Table 7 below, indicate a 14-fold increase in enzyme yield using the Bacillus subtilis (ATCC No. 31954) microorganism. These results also demonstrate a dramatic increase in the overall yield of enzyme at 25° C. vs. 40° C.

TABLE 7

| Micro-organism | Temperature (°C.) | Incubation Time (hours) | Cell Growth (g wet wt./L) | Enzyme Production | |
|---|---|---|---|---|---|
| | | | | (U/L) | (U/g wet wt.) |
| Bacillus subtilis 168 | 25 | 12 | 11.85 | 142.2 | 12.0 |
| Bacillus subtilis ATCC No. 31954 | 25 | 12 | 14.75 | 2013 | 137 |

EXAMPLE 8

Electrophoretic Patterns Differentiate Two Strains of Bacillus subtilis

This is a comparative example.

The electrophoretic patterns of esterase enzymes from Bacillus subtilis 168 and Bacillus subtilis (ATCC No. 31954), obtained using the method developed by Hendrick and Smith (Archives of Biochemistry and Biophysics, 126:155, 1968), were compared. Enzyme samples were applied to electrophoresis plates comprised of 7 percent gelatin and, after the completion of electrophoresis, were stained for esterase activity, using the method of Higerd and Spizizen cited in Example 7.

Two esterase activity bands were present in partially purified extract from the Bacillus subtilis (ATCC No. 31954) microorganism. However, extract from the Bacillus subtilis 168 strain contained only one esterase activity band. When the extracts from the two strains were co-applied to the gelatin, three distinct activity bands were obtained, clearly differentiating the enzymes from the two bacterial strains.

Although the invention has been described in considerable detail with particular reference to certain preferred embodiments thereof, variations and modifications can be effected within the spirit and scope of the invention.

We claim:

1. An enzyme which catalyzes the hydrolysis of glycerol esters and is specific for alkyl esters wherein the alkyl group or groups has from 1 to 4 carbon atoms inclusive, said enzyme being isolated from the microorganism Bacillus subtilis ATCC No. 31954.

2. A method for the production of an enzyme which catalyzes the hydrolysis of glycerol esters and is specific for alkyl esters wherein the alkyl group or groups has between 1 and 4 carbon atoms inclusive, said method comprising the steps of:
   (a) growing the microorganism Bacillus subtilis ATCC No. 31954 in a growth medium and
   (b) recovering the enzyme therefrom.

3. The method of claim 2 wherein the growth medium in step (a) is MRS medium.

4. The method of claim 2 wherein said enzyme is recovered by precipitation with an organic solvent.

* * * * *